United States Patent [19]
Faries, Jr. et al.

[11] Patent Number: 5,615,423
[45] Date of Patent: *Apr. 1, 1997

[54] SURGICAL DRAPE WITH PLACEMENT INDICIA

[75] Inventors: Durward I. Faries, Jr., McLean, Va.;
Bruce R. Heymann, Silver Spring, Md.; Mark Licata, Richmond, Va.

[73] Assignee: O. R. Solutions, Inc., Chantilly, Va.

[ * ] Notice: The term of this patent shall not extend beyond the expiration date of Pat. No. 5,333,326.

[21] Appl. No.: 597,763

[22] Filed: Feb. 7, 1996

Related U.S. Application Data

[63] Continuation-in-part of Ser. No. 399,975, Mar. 6, 1995, Pat. No. 5,522,095, which is a continuation-in-part of Ser. No. 224,378, Apr. 7, 1994, Pat. No. 5,429,801, which is a division of Ser. No. 33,639, Mar. 16, 1993, Pat. No. 5,333,326.

[51] Int. Cl.$^6$ .................................................. F25C 1/00
[52] U.S. Cl. ................................................ 4/639; 220/577
[58] Field of Search ................... 4/639; 62/66; 422/40, 422/41; 220/577; 604/113; 607/113

[56] References Cited

U.S. PATENT DOCUMENTS

| | | |
|---|---|---|
| 4,393,659 | 7/1983 | Keyes et al. . |
| 4,474,016 | 10/1984 | Winchell . |
| 4,782,835 | 11/1988 | Bernadini . |
| 4,934,152 | 6/1990 | Templeton . |
| 5,042,455 | 8/1991 | Yue et al. . |
| 5,163,299 | 11/1992 | Faries, Jr. et al. . |
| 5,331,820 | 7/1994 | Faries et al. . |
| 5,333,326 | 8/1994 | Faries et al. . |
| 5,429,801 | 7/1995 | Faries, Jr. et al. . |
| 5,457,962 | 10/1995 | Faries, Jr. et al. . |

*Primary Examiner*—John C. Fox

[57] ABSTRACT

A sterile surgical drape for use with a system for thermally treating sterile medium is accomplished by a drape including indicia symbolically directing placement of the drape over the system. The system may include a single or plurality of basins for thermally cooling and/or heating the sterile medium. The drape includes various indicia indicating which portions of the drape are placed over the corresponding portions of the thermal treatment system. The indicia may include symbols indicating the center of the basins, the direction to unfold the drape after removing the drape from its package, the proper orientation of the drape when placed on the system, and alignment of the drape on the system such that the drape overhangs the top surface of the system for a sufficient length to reduce the risk of contamination to the sterile medium. The indicia assist the operator in properly aligning and placing the drape over the system to ensure sterility.

34 Claims, 4 Drawing Sheets

SURGICAL DRAPE WITH PLACEMENT INDICIA

CROSS-REFERENCE TO RELATED APPLICATIONS

This application is a continuation-in-part of copending U.S. patent application Ser. No. 08/399,975, filed Mar. 6, 1995, which is a continuation-in-part of our U.S. Pat. No. 5,429,801 which is a division of our U.S. Pat. No. 5,333,326. The disclosures from the aforementioned copending application and patents are expressly incorporated by reference herein in their entireties.

BACKGROUND OF THE INVENTION

1. Technical Field

The present invention pertains to improvements in methods and apparatus for surgical drapes utilized in thermally treating surgical sterile fluid media. In particular, the invention is an improvement of the methods and apparatus disclosed in U.S. Pat. Nos. 4,393,659 (Keyes et al), 4,934,152 (Templeton) and copending U.S. patent application Ser. No. 08/399,975. The disclosures in those patents are expressly incorporated by reference herein in their entireties.

2. Discussion of the Prior Art

The Keyes et al patent discloses a surgical slush producing system having a cabinet with a heat transfer basin at its top surface. A refrigeration mechanism in the cabinet takes the form of a closed refrigeration loop including: an evaporator in heat exchange relation to the exterior of the heat transfer basin; a compressor; a condenser; and a refrigeration expansion control, all located within the cabinet. A separate product basin is configured to be removably received in the heat transfer basin. Spacers, in the form of short cylindrical stubs or buttons are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile sheet of material, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency in the product basin.

As noted in the Templeton patent, the above-described system has a number of disadvantages. In particular, a separate product basin must be removed and resterilized after each use. Additionally, the glycol or other thermal transfer medium is typically highly flammable or toxic and, in any event, complicates the procedure. The Templeton patent discloses a solution to these problems by constructing an entirely new apparatus whereby the product basin is eliminated in favor of the sterilized drape impervious to the sterile surgical liquid, the drape being made to conform to the basin and directly receive the sterile liquid. Congealed liquid is scraped off the sides of the conformed drape receptacle to form the desired slush.

In addition, Templeton also provides an electrical heater disposed at the bottom of the basin to convert the sterile slush to warmed liquid, or to heat additional sterile liquid added to the basin. Templeton describes the need for such warmed sterile liquid as occurring after a surgical procedure is completed to facilitate raising the body cavity of the surgery patient back to its normal temperature by contact with the warm liquid.

The present invention is an improvement in the drape disclosed in copending U.S. patent application Ser. No. 08/399,975. The thermal treatment system disclosed in that application includes a plurality of basins adjacent each other for producing sterile slush and heating a sterile liquid respectively. A surgical drape is sufficiently large to be placed over the thermal treatment system and is pushed down into the basins to form drape receptacles for containing the sterile liquid. The drape includes centering indicia for indicating the centers of the basins wherein surrounding portions of the drape adjacent the centering indicia are pushed into the basins until the centering indicia reside at the approximate center of the lowermost portion or bottom of the basin in order to form the drape receptacles. However, the drape including centering indicia lacks the desired capability of directing proper initial placement of the drape on the thermal treatment system. In particular, the centering indicia do not indicate the proper orientation or alignment of the drape on the top surface of the thermal treatment system and therefore the drape may not uniformly cover the thermal treatment system, thereby risking possible contamination of the sterile liquid. The centering indicia also do not indicate the proper direction and sequence in which to unfold the drape once the drape is removed from a package, thereby often requiring the drape to be refolded and realigned. Further, the centering indicia do not provide guidance as to the proper length of the drape overhanging the top surface of the thermal treatment system and therefore may increase the risk of contamination to the sterile liquid due to improper placement of the drape.

OBJECTS AND SUMMARY OF THE INVENTION

Accordingly, it is an object of the present invention to provide a surgical drape for use with a system for thermally treating a sterile medium wherein the drape includes indicia designating proper orientation of the drape to assist an operator in properly aligning the drape on the system housing and ensure sterility of the sterile medium.

It is another object of the present invention to provide a surgical drape for use with a system including a plurality of basins for cooling and/or heating a sterile medium wherein the drape bears indicia locating the approximate centers of the basins in order to assist an operator in placing the surgical drape over the system cabinet and in the basins to maintain sterility of the sterile medium.

Yet another object of the present invention is to provide a surgical drape for use with a system for thermally treating a sterile medium wherein the drape includes indicia signifying the direction in which to unfold the drape after removing the drape from its package.

Still another object of the present invention is to provide a surgical drape for use with a system including a basin for thermally treating a sterile medium wherein the drape has various indicia signifying both proper alignment of the drape over a top surface of the system and the portion of the drape to be disposed in the basin. The indicia assist an operator in placing the drape over the system such that the drape overhangs the top surface by a sufficient length in order to maintain sterility of the sterile field.

A further object of the present invention is to provide a surgical drape for use with a system including a basin for thermally treating a sterile medium wherein the drape bears indicia designating the approximate center of the basin in order to assist an operator in placing the drape over the system and in the basin to maintain sterility of the sterile field.

The aforesaid objects are achieved individually and in combination, and it is not intended that the present invention be construed as requiring two or more of the objects to be combined unless expressly required by the claims attached hereto.

According to the present invention, a surgical drape bears a plurality of indicia symbolically directing the proper placement of the drape over a thermal treatment system. The system typically includes at least one basin for thermally treating a sterile medium. The drape is placed over the system housing such that a portion of the drape is pushed down into each basin forming drape receptacles for containing the sterile medium. The remaining area of the surgical drape covers or drapes the system housing. The drape may include various indicia for assisting an operator in correctly placing the drape over the system. Specifically, the indicia may direct the operator as to the proper orientation of the drape, proper alignment of the drape on a top surface of the system for sufficient overhang of the surgical drape to maintain sterility, the location of the drape relative to the center of each basin cooling or heating the sterile medium in order for proper portions of the drape to be pushed down into each basin, and the direction to unfold the drape when initially removed from the package and placed on the system. Once the operator has placed the surgical drape over the system housing such that the indicia are coincident their corresponding locations relative to the system housing, the drape is properly placed and aligned on the thermal treatment system to ensure sterility of the sterile medium.

The above and still further objects, features and advantages of the present invention will become apparent upon consideration of the following detailed description of a specific embodiment thereof, particularly when taken in conjunction with the accompanying drawings when like reference numerals in the various figures are utilized to designate like components.

DESCRIPTION OF THE PREFERRED EMBODIMENTS

Figure 1:
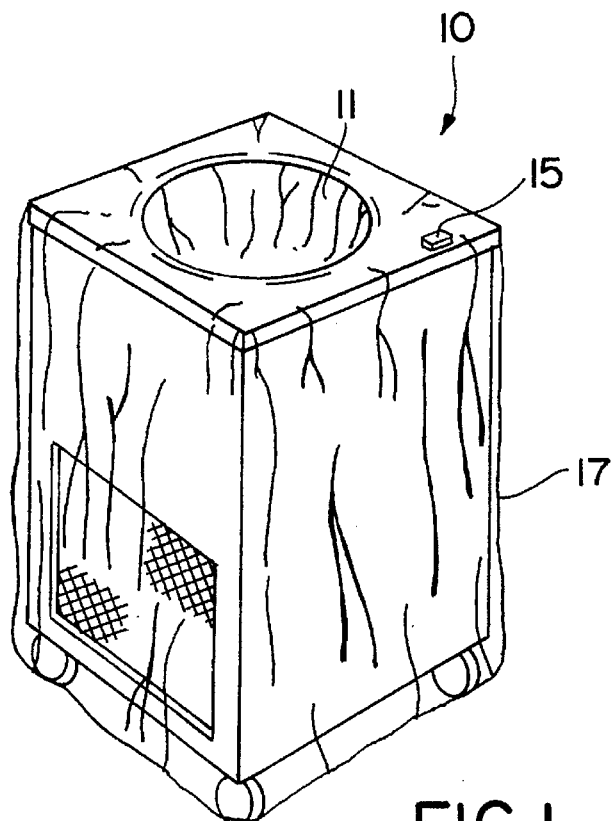
FIG. 1 is a view in perspective of a thermal treatment system of the type employed in the present invention.

Referring to FIG. 1 of the accompanying drawings, a thermal treatment system of the type described in the above-referenced Templeton patent includes a housing or cabinet 10 with a top surface having a basin 11 mounted thereon in an appropriately sized recess. Basin 11 is made of thermally conductive material, typically stainless steel, and includes a generally flat bottom wall and a frusto-conical side wall. A conventional refrigeration unit is disposed within cabinet 10 and typically includes a compressor, a condenser and an expansion control unit connected by appropriate fluid conduits in a closed refrigeration loop with an evaporator (not shown). The evaporator is in the form of a coil wound about the exterior surface of basin 11 in thermal transfer relation therewith. In response to the refrigeration unit being activated via appropriate controls 15, the evaporator cools the side wall of basin 11 to a temperature substantially below the freezing temperature of a sterile liquid disposed in basin 11 thereby forming sterile slush. This temperature is preferably on the order of −32° F. to 10° F. For further details of the structure and operation of the refrigeration unit, reference is made to the aforementioned Keyes et al and Templeton et al patents.

A sterile drape 17, preferably transparent, is disposed over the top and sides of cabinet 10 and made to conform to the side wall and bottom of basin 11. The portion of drape 17 disposed in the basin serves as a sterile receptacle for sterile liquid placed therein to be frozen into the desired sterile slush. Typical sterile liquid used for this purpose is a 0.80% to 0.95% sodium chloride solution (i.e., saline). Drape 17 is made from material that is impervious to the sterile liquid and sufficiently soft and pliable to readily conform to the basin wall. The drape may also have a preformed section contoured to match the contour of the basin. The thickness of the drape is preferably minimized to render thermal transfer therethrough most efficient, yet the thickness is sufficient to resist tearing and puncturing during normal use. Typically, by way of example only, drape 17 may be made of materials commonly used in hospitals for surgical drapes and has a thickness in the range of 3.0 to 10.0 mils. Drape 17 may also be made of polyurethane film as disclosed for the drape in the aforementioned Templeton patent. Further, the shape of drape 17 is substantially that of a square of greater size than the square top surface of the thermal treatment system cabinet; however, drape 17 may be substantially rectangular or any other shape to provide a better fit and accommodate various shaped cabinets. Moreover, the drape is designed to be disposable after a single use and is provided presterilized and prepackaged to preserve its sterile state during storage. When the thermal treatment system is operating, the sterile liquid in the drape container freezes in pieces on the side walls of the container.

Figure 4A:
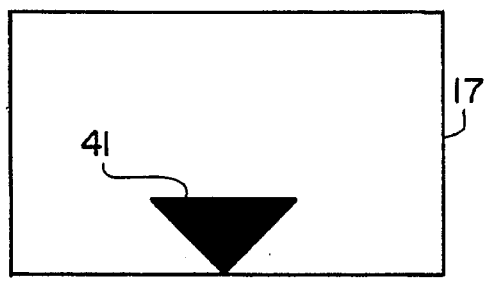
FIGS. 4A, 4B are views in plan of surgical drapes bearing indicia symbolically designating the proper direction to unfold the drape according to the present invention.
Figure 4B:
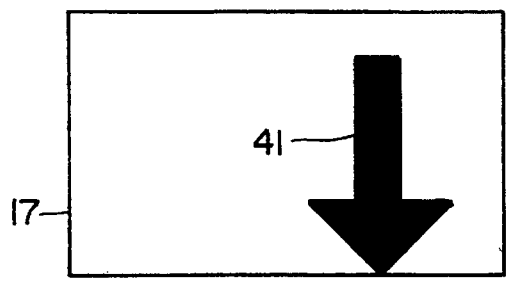

Another sterile drape, suitable for covering the top surface of a thermal treatment system substantially similar to the system described above (FIG. 1) and including indicia for symbolically directing a user in unfolding the drape when removed from its package is illustrated in FIGS. 4A–4B. Specifically, drape 17 is substantially similar to the drape described above except that drape 17 further includes symbolic indicia for assisting an operator to properly unfold drape 17 into the proper orientation for placement over the thermal treatment system. Initially, drape 17 is folded in order to be efficiently and securely stored in packaging for preservation of its sterile state during shipment, distribution and storage. When a nurse or other operating room personnel opens the drape package, indicia 41 disposed on a folded side of drape 17 and visible to the nurse, indicate the position or direction to unfold drape 17 for proper orientation and placement over the thermal treatment system cabinet. Indicia 41 may be any shape or symbol indicating the position or direction for unfolding. Typically, indicia 41 include an unshaded triangle substantially similar to the head of an arrow pointing toward the intended unfolding direction. Alternatively, indicia 41 may include a shaded full bodied arrow, substantially similar in shape to the arrows on one-way street signs, pointing toward the unfolding direction.

Referring to FIGS. 3A–3F, orientation indicia may also be disposed on a sterile drape in order to assist the operator in properly orientating the drape relative to a basin of a thermal treatment system. Specifically, drape 17 is substantially similar to the drape having unfolding indicia as described above except that drape 17 also or only includes indicia for properly orienting the drape. Orientation indicia 43 are typically disposed at the approximate center of drape 17 for use with machines having centered basins, and preferably have the shape of the particular basin utilized in the thermal treatment system. For basins that are not centered on the top of a cabinet, indicia 43 would similarly not be centered on the drape. The basin of the thermal treatment system may be of any shape (i.e. typically rectangular, polygonal, oval or circular) and therefore the configurations of the orientation indicia 43 preferably vary in accordance with the shape of the particular basin. Although the periphery of each drape illustrated in FIGS. 3A–3F is a larger version of the shape of indicia 43 and hence the basin to be covered, such is not necessarily the case (i.e., circular symbol 43 can be used with a square drape, etc.). The size of indicia 43 may be the same as the basin size but is preferably much smaller and positioned to be centered in the basin when the drape is pushed into and conforms to the basin. As shown, indicium or symbol 43 is a miniaturized shaded version of the basin but may be an unshaded outline positioned to be placed at the approximate center of the basin.

In order to reduce the risk of contamination that would result if a sterile drape is not positioned properly on a top surface of a thermal treatment system cabinet, the drape may include indicia for proper center, corner or edge alignment of the drape on the top surface as illustrated in FIGS. 7A–7K. Specifically, drape 17 is substantially similar to the drapes as described above except that drape 17 includes indicia for properly aligning the drape with respect to the center, corners or edges of the top surface of a cabinet such that the drape uniformly overhangs the top surface by a length sufficient to maintain sterility of the sterile field and does not inadvertently move relative to the cabinet. These alignment indicia are typically disposed symmetrically at or about the approximate center and on the non-solution receiving side of drape 17 for greater visibility to the nurse. The alignment indicia are intended to be positioned along respective edges or corners or at the center of the top surface of the cabinet or the basin to allow for proper overhang of drape 17. The alignment indicia may include several variations of symbols to direct the operator toward the proper alignment of the drape.

For example, drape 17 may include alignment indicia disposed at the approximate center of the drape, usually to facilitate placing of that indicia at the approximate center of the basin. Specifically, special symbols 45, typically an "X" or star (FIGS. 7B and 7A, respectively), may be placed at the approximate center of the drape. Surrounding portions of drape 17 adjacent special symbols 45 are pushed down into the basin subsequent to placement of drape 17 on the top surface of the cabinet. Once the drape portion bearing special symbols 45 is pushed down into and positioned at the approximate center of the lowermost portion or bottom of the basin, drape 17 overhangs the top surface of the cabinet uniformly in all directions by a sufficient length to maintain sterility of the sterile field. In certain instances, depending upon the particular thermal treatment system being employed, a bolt or plug may reside at the approximate center of the lowermost portion or bottom of the basin. In these instances, special symbols 45 may be positioned coincident the bolt or plug for proper placement of drape 17 over the cabinet. In the absence of any such center indications in the basin, the operator must estimate the location of the approximate center of the basin for aligning the special symbols 45.

Another variation of the alignment indicia may include nested symbols indicating perimetric edges and corners of the basin and top surface of the cabinet. Specifically, symbol 47 (FIG. 7C) includes an outer symbol outlining the perimeter of the top surface of the cabinet and an inner symbol 48 outlining the basin periphery. Symbol 51 (FIG. 7E) represents the location of one of the peripheral corners of the top surface and takes the form of a small shaded triangle at the intersection of the two edges forming the corner. The basin periphery itself is shown in dashed lines in FIG. 7E. The inner symbol 52 represents an outline of the basin periphery. The outlines 47, 48 of the perimeter of the top surface and basin, respectively. are slightly larger than the corresponding actual features in order to subsequently be positioned coincident the actual features once portions of the drape have been pushed down into the basin as described below. Similarly and for the same reasons, the outline 51 of the corner of the top surface is positioned slightly beyond the actual corner. Proper alignment of drape 17 occurs after orientation and placement of the drape on the top surface of the cabinet. A portion of the drape residing within the inner symbols 48, 52 of the nested symbols is pushed down into the basin until the inner and outer symbols are coincident with corresponding features on the top surface of the cabinet.

Alternatively, the alignment indicia may indicate the top surface of the thermal treatment system by including a series of four corner symbols 49 (FIG. 7D) each outlining the intersection of a respective pair of edges forming a respective corner of the top surface of the cabinet. Symbol 49 outlines a small fraction of each respective edge immediately adjacent the intersection forming the corner where the fractional portions of the edges outlined are substantially similar in length. Symbols 49 thus designate the corner boundaries of the cabinet top surface. The actual basin periphery is shown in dashed lines in FIG. 7D.

Further, the alignment indicia may also include one or more symbols 59 (FIG. 7K) substantially similar to the letter "T", each having its crossbar portion positioned to be centered on and extend along a shod length of a respective peripheral cabinet edge. The perpendicular leg extends from the approximate center of the crossbar toward the center of the drape. The crossbar and perpendicular leg are preferably substantially the same length and are a fraction of the length of the corresponding edge of the top surface of the cabinet.

Figure 7C:
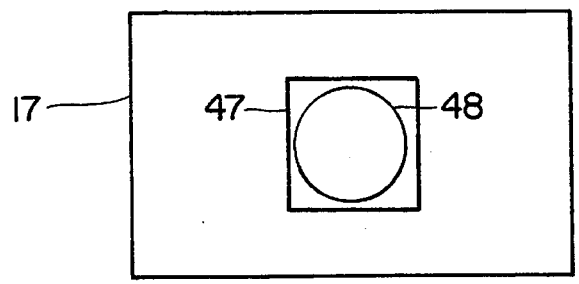
Figure 7D:
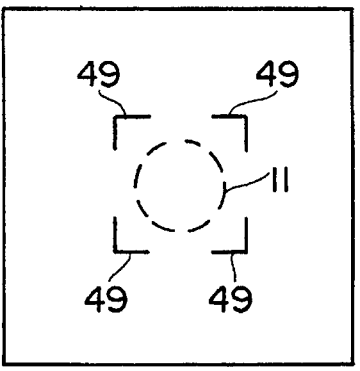
Figure 7H:
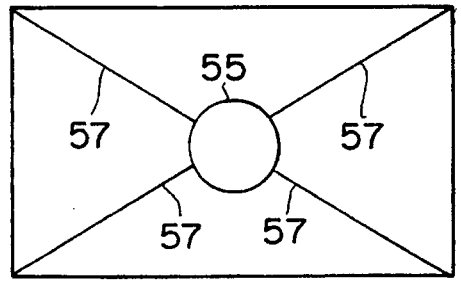
Figure 7E:
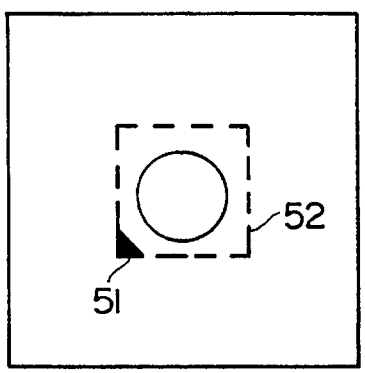
Figure 7I:
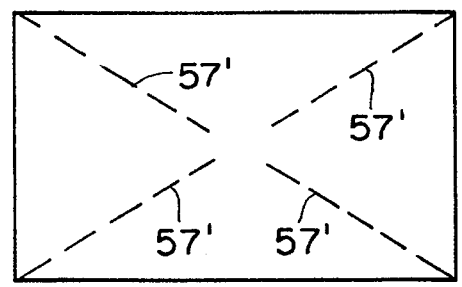
Figure 7F:
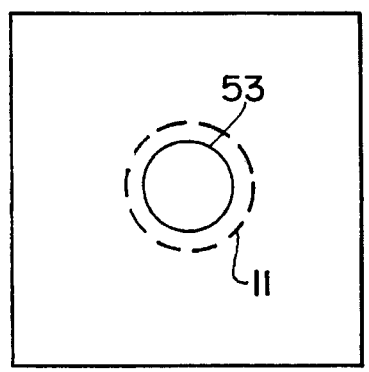
Figure 7J:
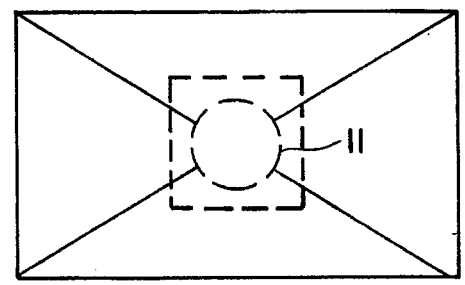
Figure 7G:
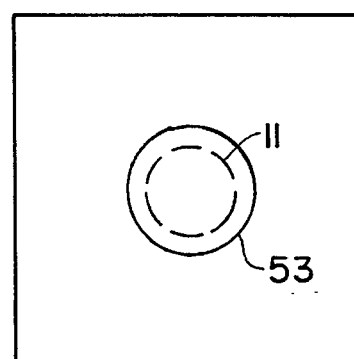
Figure 7K:
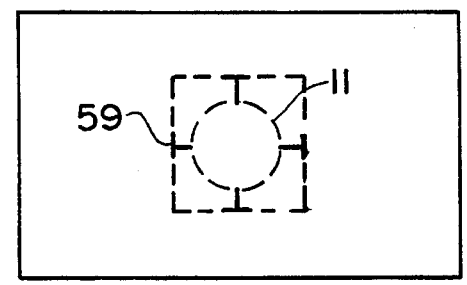

The actual cabinet and basin peripheries are shown in dashed lines in FIG. 7K for ease of reference. Symbols 49, 59 are disposed slightly beyond and designate boundaries slightly larger than the top surface of the thermal treatment system in order to be subsequently positioned coincident the actual features when a portion of the drape being pushed down into the basin as described below. Drape 17 is aligned in a substantially similar manner as described above by determining the orientation of the drape and placing the drape over the top surface of the thermal treatment system in order to push a portion of the drape surrounded by symbols 49 or 59 into the basin until symbols 49 or 59 respectively reside coincident a corresponding corner or midpoint of an edge of the top surface of the thermal treatment system.

Yet another variation of the alignment indicia may include basin indicia 53 (FIGS. 7F and 7G) having an outline of either the uppermost (FIG. 7G) or lowermost (FIG. 7F) portion of the basin. The outline of the uppermost portion is slightly larger than the actual basin in order to be subsequently positioned coincident the basin in response to a portion of the drape being disposed within the basin as described below. The dashed line circle represents the actual uppermost basin periphery in FIG. 7F, and the actual lowermost basin periphery in FIG. 7G, for ease of reference. Drape 17 is aligned by determining the orientation of the drape and subsequently placing the drape over the top surface of the thermal treatment system. The portion of drape 17 within the outline of the basin is pushed down into the basin until either the outline of the lowermost or uppermost portion of the basin is coincident the corresponding portion of the basin.

Still another variation of the alignment indicia may include a series of substantially diagonal lines 57 (FIG. 7H). Substantially diagonal lines 57 originate from respective corners of drape 17 and extend diagonally toward the center of the drape until reaching an outline 55 of the basin. The outline of the basin is preferably slightly larger than the actual basin in order to be subsequently positioned coincident the basin periphery when the portion of the drape within the basin outline 55 is pushed down into and conforms to the basin. Substantially diagonal lines 57 and the outline of the basin may be imprinted on the drape, for example, using solid lines. Drape 17 is aligned by determining the orientation of the drape and placing the drape over the top surface of the system cabinet such that lines 57 extend inwardly from corresponding corners of the top surface. Portions of drape 17 within the outline of the basin are pushed down into the basin until the outline 55 of the basin is coincident the basin.

Alternatively, the alignment indicia may be substantially similar to diagonal lines 57 and the outline of the basin as described above except that only the diagonal lines 57 are present. In this instance, diagonal lines 57 or 57' may be imprinted on the drape using solid or dotted lines, respectively (FIGS. 7J, 7I, respectively), and extend from respective corners of the drape toward the drape center. The peripheries of the actual cabinet and basin are shown in dashed lines in FIG. 7J for ease of reference to this description.

Figure 2:
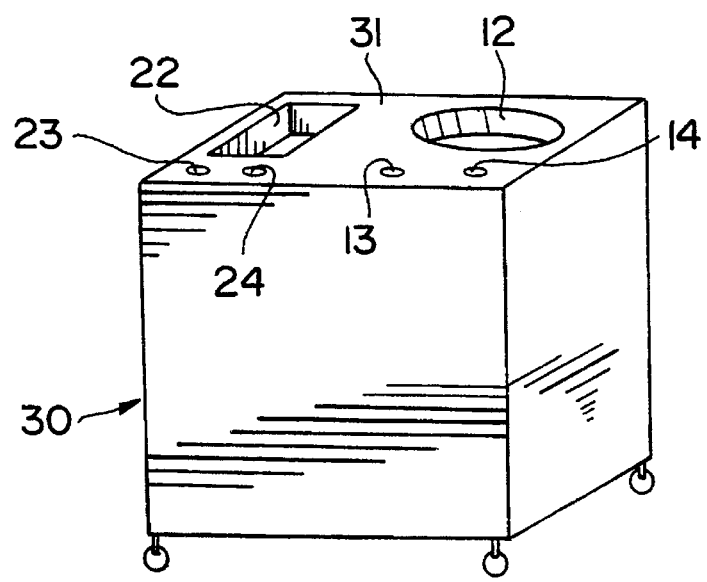
FIG. 2 is a view in perspective of a thermal treatment system including a plurality of basins for heating and cooling a sterile medium of the type employed in the present invention.
Figure 3A:
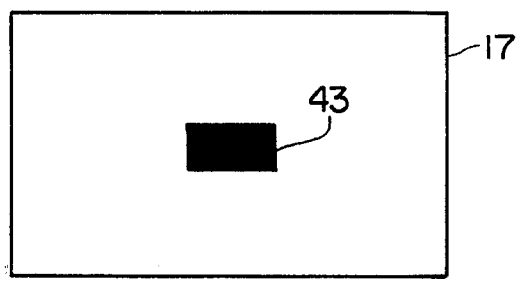
FIGS. 3A–3F are views in plan of surgical drapes bearing indicia designating the orientation and center of the drape in order to assist an operator in the proper placement of the drape over the system of FIG. 1 according to the present invention.
Figure 3B:
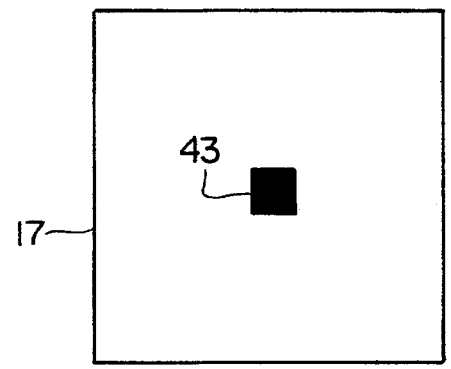
Figure 3C:
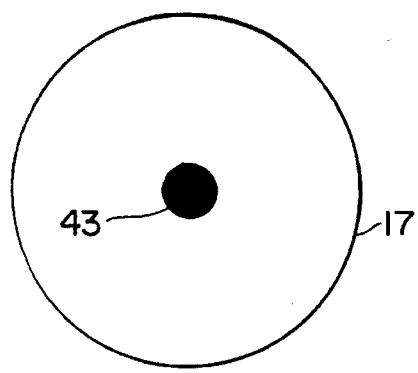
Figure 3D:
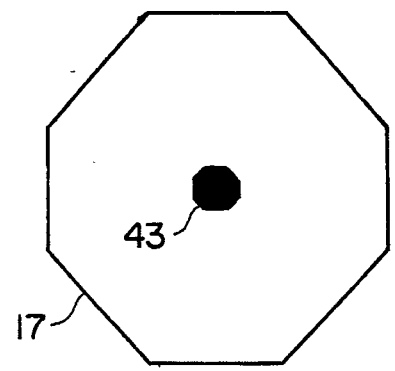
Figure 3E:
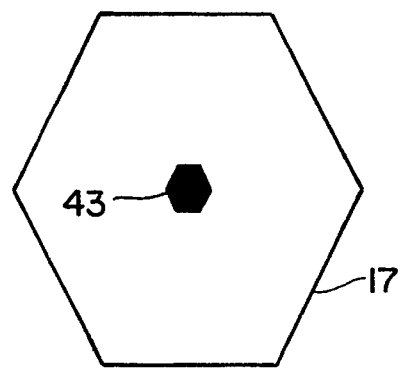
Figure 3F:
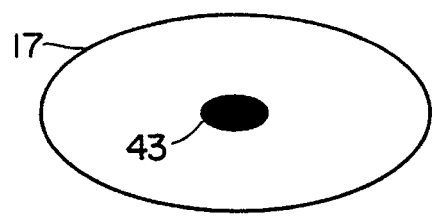
Figure 5:
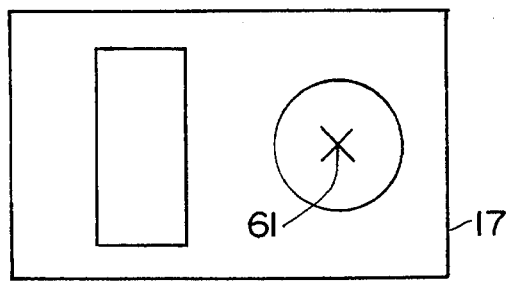
FIG. 5 is a view in plan of a surgical drape bearing indicia located at the drape portions to be placed at the center of a basin for cooling or heating sterile medium in order to assist an operator in the proper placement of the drape over the system of FIG. 2 according to the present invention.
Figure 7A:
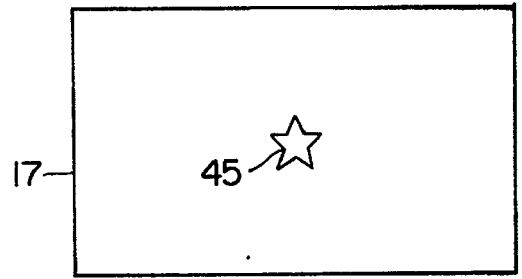
FIGS. 7A–7K are views in plan of surgical drapes bearing indicia symbolically designating proper alignment of the drape over a top surface of the system of FIG. 1 in order for the drape to overhang the top surface by a sufficient length to maintain sterility according to the present invention.
Figure 7B:
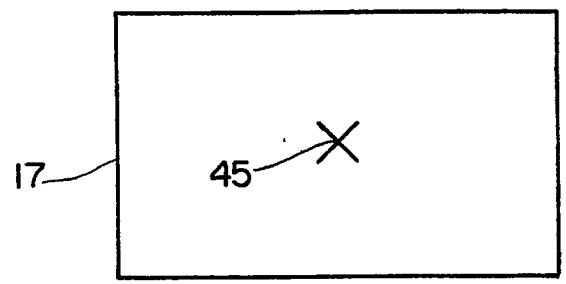
Figure 6:
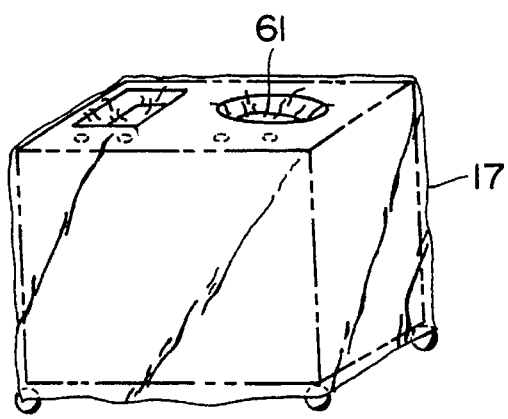
FIG. 6 is a view in perspective of the drape of FIG. 5 positioned over the system of FIG. 2.

A surgical drape with indicia suitable for use with a thermal treatment system having a plurality of basins is illustrated with reference to FIGS. 2, 5 and 6. Initially, a thermal treatment system having multiple basins for simultaneously cooling and heating sterile liquid has an integral assembly 30 including a slush basin 12 for slush phase medium and a warming basin 22 for heated liquid phase medium recessed into top surface 31 of a common cabinet. Also disposed in top surface 31 are a cooling unit power switch 13, a cooling unit temperature controller/indicator 14, a heater power switch 23 and a heater unit temperature controller/indicator 24. For further details of the structure and operation of assembly 30, reference is made to the aforementioned copending U.S. patent application Ser. No. 08/399,375.

A drape 17 for use with the plural basin system is substantially similar to the drapes described above but is of sufficient size to encompass the plurality of basins. Specifically, drape 17 may include alignment indicia substantially similar to any of the aforementioned alignment indicia as described above. The alignment indicia are typically present for only basins cooling the sterile medium and/or producing slush. However, the alignment indicia may be present for all basins of the plural basin system to ensure consistent alignment. For example, the alignment indicia may include cooling basin indicia 61 (FIGS. 5,6) which are substantially similar to special symbols 45 (FIGS. 7A–7B) as described above. Cooling basin indicia 61 indicate the approximate center of only the cooling basins and are not necessarily disposed at the approximate center of drape 17. This allows drape 17 to achieve optimal positioning in the cooling basin while ensuring that the drape overhangs the top surface of the plural basin system by a sufficient length to maintain sterility and not interfere with vents on the sides of the plural basin system. Drape 17 is aligned by determining the proper orientation of the drape and placing the drape over the top surface of the plural basin system in order to push portions of the drape coincident the basins down into each of the basins until cooling basin indicia 61 are properly positioned at the approximate center of the lowermost portion or bottom of the cooling basins. Further, drape 17 may accommodate any number of heated and cooled basins in a thermal treatment system in substantially the same manner as described above. Moreover, drape 17 for the plural basin system may include any of the above-mentioned orientation, fold, alignment or other indicia implemented in a substantially similar manner as respectively described above.

Several techniques may be employed to dispose the indicia on the drape. For example, the outlines of the top surfaces and basins of the thermal treatment systems may be accomplished by sealing creases or folds in the drape material. Further, all indicia may be affixed to the drape by use of striping, dye, printed film or any other known marking or affixation techniques. Moreover, the drape may include one or more of the aforementioned indicia in any combination or permutation. In addition, the aforementioned indicia may be disposed on a drape typically having a size greater than needed for the thermal treatment system. The operator aligns the drape on the thermal treatment system in a substantially similar manner for the respective indicia as described above and, if necessary, may cut the drape to an appropriate length for the specific thermal treatment system employed. The drape may therefore be compatible with numerous thermal treatment systems and ensures a consistent length and fit.

It will be appreciated that the embodiments described above and illustrated in the drawings represent only a few of the many ways of implementing a surgical drape with placement indicia.

The drape may include any material capable of collecting sterile medium (i.e., impervious to liquid) and maintaining sterility. Further, the drape may be constructed to be utilized for any number of basins and include the corresponding indicia.

The indicia may be any indicia capable of being affixed to the drape and readily visible. Further, the indicia may be removably or permanently affixed to the drape by processes including but not limited to glue or other adhesive material, formed as part of the drape, painted, drawn or imprinted on the drape, or any other known affixation method. Moreover, the indicia may be constructed from any material that does not contaminate the sterile medium. In addition, the indicia may include any symbols, characters, words etc. indicating the proper positioning of the drape on a thermal treatment system and is not limited to the specific symbols disclosed herein.

From the foregoing description it will be appreciated that the invention makes available a novel surgical drape wherein the drape has indicia indicating proper placement of the drape over a thermal treatment system thermally treating a sterile medium.

Having described preferred embodiments of a new and improved surgical drape having placement indicia, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A surgical drape for use in a thermal treatment system for thermally treating a sterile medium and including a basin recessed in a top surface of a system housing for collecting said sterile medium, said drape ensuring the sterility of said sterile medium and comprising:

a drape portion for covering and hanging down from said top surface of said system housing; and indicia affixed to said drape symbolically directing placement of said drape portion over said top surface.

2. The drape of claim 1 wherein said indicia include orientation indicia designating the proper orientation of the drape on said top surface.

3. The drape of claim 2 wherein said orientation indicia include an outline of the basin.

4. The drape of claim 3 wherein said orientation indicia further include a centering indicia in the shape of said basin and disposed within said outline indicating the center of the basin.

5. The drape of claim 1 wherein said indicia include centering indicia indicating the center of said basin and the drape portion to be pushed down into said basin such that said centering indicia resides at the center of said basin.

6. The drape of claim 5 wherein:

said system further includes a plurality of basins recessed in said top surface, at least one of said basins for cooling said sterile medium and at least another of said basins for heating said sterile medium; and said centering indicia designating the center of only said basins for cooling said sterile medium.

7. The drape of claim 1 wherein said indicia include alignment indicia designating the drape portion to be placed over said top surface such that said drape overhangs said top surface by a length sufficient to ensure sterility.

8. The drape of claim 7 wherein said alignment indicia include an outline of said basin.

9. The drape of claim 8 wherein said outline is of an uppermost portion of said basin and said alignment indicia include symbols for indicating the drape portion to be positioned on a corresponding corner of said system.

10. The drape of claim 8 wherein said alignment indicia include diagonal lines extending from corresponding corners of said drape to said outline.

11. The drape of claim 8 wherein said alignment indicia further include an outline of the edges of said top surface.

12. The drape of claim 7 wherein said alignment indicia include symbols indicating the centerpoint of each of the edges of said top surface.

13. The drape of claim 7 wherein said alignment indicia include diagonal lines extending from each corner of said drape toward the center of said drape.

14. The drape of claim 7 wherein said alignment indicia include symbols indicating the corners of said top surface.

15. The drape of claim 8 wherein said outline is of an uppermost portion of said basin.

16. The drape of claim 8 wherein said outline is of a lowermost portion of said basin.

17. The drape of claim 1 wherein said indicia include fold indicia designating the direction the drape is to be unfolded for proper orientation on the system.

18. The drape of claim 17 wherein said fold indicia includes a triangular indicium.

19. The drape of claim 17 wherein said fold indicia includes an arrow.

20. The drape of claim 1 further including:

an excess portion adjacent said drape portion wherein said excess portion is cut from said drape when said drape portion adequately covers said system.

21. In a thermal treatment system including a basin for containing a sterile medium and a sterile drape having indicia for directing placement of said drape over a top surface of said system, a method of installing said drape on said top surface comprising the steps of:

(a) placing said drape over said top surface;

(b) aligning and placing said indicia over corresponding portions of said top surface;

(c) pushing portions of said drape coincident said basin into said basin such that said drape conforms to said basin and forms a drape receptacle for containing said sterile medium.

22. The method of claim 21 wherein said indicia include unfolding indicia designating the direction to unfold said drape for proper orientation on said top surface, and wherein step (a) further includes:

(a.1) removing said drape from said package and unfolding said drape on said top surface in the direction indicated by said unfolding indicia.

23. The method of claim 21 wherein said indicia include a centering indicium indicating the center of said basin, and step (b) further includes:

(b.1) aligning said centering indicium over the center of said basin; and step (c) further includes:

(c.1) pushing portions of said drape coincident said basin into said basin until said centering indicium is positioned at the center of the bottom of said basin.

24. The method of claim 21 wherein said system further includes a plurality of basins, a portion of said basins for cooling said sterile medium and others of said basins for heating said sterile medium, wherein said indicia include centering indicia indicating the center of said basins for cooling said sterile medium, and step (b) further includes:

(b.1) aligning said centering indicia over the centers of respective basins cooling said sterile medium; and step (c) further includes:

(c.1) pushing portions of said drape coincident said plurality of basins into said plurality of basins until said centering indicia are positioned at the center of the bottom of said basins cooling said sterile medium.

25. The method of claim 21 wherein said indicia include orientation indicia in the shape of said basin, and wherein:

step (a) further includes:
- (a.1) manipulating said drape such that said orientation indicia correspond to the orientation of said basin;

step (b) further includes:
- (b.1) aligning said orientation indicia with said basin.

26. The method of claim 21 wherein said indicia include alignment indicia indicating the drape portion to be placed on a top surface of said system, and step (b) further includes:
- (b.1) aligning said alignment indicia on the corresponding portion of the top surface of said system; and step (c) further includes:
- (c.1) pushing portions of said drape coincident said basin into said basin until said alignment indicia are coincident respective portions of said system.

27. The method of claim 21 further including the step of:
- (d) cutting the drape to an appropriate length to accommodate said system.

28. A method for directing placement of a drape over a top surface of a thermal treatment system having a basin for containing a sterile medium, said method comprising the steps of:
- (a) forming a surgical drape configured to overlie the top surface of the system with a portion of the drape recessed into the basin to define a drape container in the basin for the sterile medium; and
- (b) disposing indicia on said drape to direct a user of the drape in properly aligning and placing the drape on the top surface of the system.

29. The method of claim 28 wherein step (b) further includes:
- (b.1) disposing indicia on said drape to direct a user of the drape in properly unfolding said drape in a proper orientation for placement of said drape on the system after removing said drape from a package.

30. The method of claim 28 wherein step (b) further includes:
- (b.1) disposing centering indicia on said drape indicating the center of the basin such that said drape is properly aligned on the system when said centering indicia are positioned at the center of the bottom of the basin.

31. The method of claim 28 wherein said system further includes a plurality of basins, a portion of said basins for cooling said sterile medium and others of said basins for heating said sterile medium, wherein step (b) further includes:
- (b.1) disposing centering indicia on said drape indicating the center of the basins for cooling the sterile medium such that said drape is properly aligned on the system when said centering indicia are positioned at the center of the bottom of the respective basins cooling the sterile medium.

32. The method of claim 28 wherein step (b) further includes:
- (b.1) disposing orientation indicia on said drape indicating the orientation of the drape relative to the basin to direct a user of the drape in properly aligning and placing the drape on the top surface of the system.

33. The method of claim 28 wherein step (b) further includes:
- (b.1) disposing surface alignment indicia on said drape indicating the drape portion to be placed on the top surface of the system such that said drape is properly aligned on the system when said surface alignment indicia are coincident corresponding features of the top surface after pushing portions of said drape into the basin.

34. The method of claim 28 wherein step (a) further includes:
- (a.1) forming said drape to have a length in excess of that required to cover the system such that said drape is cut to an appropriate length to accommodate the system after being placed on the system.

* * * * *